United States Patent [19]
Ridgway et al.

[11] Patent Number: 5,377,008
[45] Date of Patent: Dec. 27, 1994

[54] INTEGRATED OPTICAL COMPENSATING REFRACTOMETER APPARATUS

[75] Inventors: Richard W. Ridgway, Westerville; Anthony A. Boiarski, Columbus; Van E. Wood, Delaware; James R. Busch, Columbus, all of Ohio

[73] Assignee: Battelle Memorial Institute, Columbus, Ohio

[21] Appl. No.: 862,494

[22] Filed: Apr. 2, 1992

Related U.S. Application Data

[63] Continuation-in-part of Ser. No. 585,438, Sep. 20, 1990, Pat. No. 5,173,747.

[51] Int. Cl.$^5$ ............................................. G01B 9/02
[52] U.S. Cl. .................................. 356/361; 356/128; 356/345; 356/133; 385/12
[58] Field of Search .............. 356/345, 361, 128, 133; 385/12, 14, 13; 250/227.14, 227.19, 227.24, 227.25, 227.27, 227.28

[56] References Cited

U.S. PATENT DOCUMENTS

| | | | |
|---|---|---|---|
| 4,187,025 | 2/1980 | Harmer | 356/133 |
| 4,564,292 | 1/1986 | Omet | 356/133 |
| 4,608,344 | 8/1986 | Carter et al. | 436/34 |
| 4,650,329 | 3/1987 | Barrett et al. | 356/345 |
| 4,693,543 | 9/1987 | Matsumura et al. | 385/14 |
| 4,815,843 | 3/1989 | Tiefenthaler et al. | 356/128 |
| 4,909,990 | 3/1990 | Block et al. | 422/82.11 |
| 4,940,328 | 7/1990 | Hartman | 356/345 |
| 4,950,074 | 8/1990 | Fabricius et al. | 356/133 |
| 4,989,979 | 2/1991 | Buckman | 356/345 |
| 5,120,131 | 6/1992 | Lukosz | 356/361 |
| 5,173,747 | 12/1992 | Boiarski et al. | 356/361 |

FOREIGN PATENT DOCUMENTS

| | | |
|---|---|---|
| 0108527 | 10/1983 | European Pat. Off. |
| 3415242 | 10/1985 | Germany |
| 3723159 | 1/1988 | Germany |
| 3920840 | 6/1990 | Germany |
| 3929340 | 3/1991 | Germany |
| 2228082 | 8/1990 | United Kingdom |
| 8603004 | 5/1986 | WIPO |
| 9205429 | 4/1992 | WIPO |

OTHER PUBLICATIONS

Development of an Optical Waveguide Interferometric Immunosensor; R. G. Heideman et al; Sensors and Actuators B, 4 (1991); pp. 297-299.

An Integrated Optical Sensor for Measuring Glucose Concentration; Y. Liu et al; Applied Physics B: Photo--physics and Laser Chemistry, B54 (1992) Jan., No. 1, Berlin, DE; pp. 18-23.

*Primary Examiner*—Samuel A. Turner
*Attorney, Agent, or Firm*—Klaus H. Wiesmann

[57] ABSTRACT

An apparatus useful in immunoassay of a fluid, light is directed to an optical sensor wherein the light is transmitted to a replaceable optical device that is responsive to index of refraction in a sensing region thereof that is exposed to the fluid. One portion of the light is transmitted via a compensation path that includes the sensing region to a first detector. Another portion of the light is transmitted via a sensing path that includes the sensing region to another detector. In one embodiment a ratioing device receives an output from each detector and provides a signal responsive to the ratio of the outputs. The replaceable optical device typically comprises a pair of channel waveguides in directional coupling arrangement, or a pair of channel waveguides in an interferometer arrangement, or a ridge waveguide having a curved or serpentine path configured so that nonspecific sensing effects are compensated.

33 Claims, 10 Drawing Sheets

INTEGRATED OPTICAL COMPENSATING REFRACTOMETER APPARATUS

The present application is a continuation-in-part of application Ser. No. 07/585,438, filed Sep, 20, 1990, now issued U.S. Pat. No. 5,173,747, the disclosure of which is incorporated by reference as if completely rewritten herein.

FIELD

This invention relates to methods and apparatus useful in determining the properties of fluids. Among its uses are the chemical assay and immunoassay of a fluid particularly where nonspecific effects cause measurement errors. Further uses allow the determination of fluid properties with new optical sensors as revealed herein. In typical embodiments of the invention, light is directed to an optical sensor wherein the light is transmitted to a replaceable optical device that is responsive to index of refraction in a sensing region thereof that is exposed to the fluid. In one embodiment of the invention one portion of the light is transmitted via a compensation path that includes the sensing region to a first detector while another portion of the light is transmitted via a sensing path that includes the sensing region to another detector. In one embodiment a ratioing device receives an output from each detector and provides a signal responsive to the ratio of the outputs. The replaceable optical device typically comprises a pair of channel waveguides in directional coupling arrangement, or a pair of channel waveguides in an interferometer arrangement, or a ridge waveguide having a curved or serpentine path configured so that nonspecific effects that cause errors are compensated.

Typical embodiments of the invention comprise integrated optics devices for determination of chemicals in assays, for following the progress of reactions, immunoassay of whole blood or other body fluids, typically including low cost, disposable sensors in channel waveguide configurations such as serpentine multimode waveguides, curved single mode waveguides, single mode waveguides in coupler configurations, and single mode waveguides in interferometer configurations.

BACKGROUND

There is need for low cost, rapid, and accurate means for quantitative analysis of whole blood and other body fluids in medical diagnostics.

Some of the methods representative of the current state of the art have been recently reviewed by Bluestein, et al., (Bluestein, B. I., Walczak, I. M., and Chen, S., "Fiber Optic Evanescent Wave Immunosensors for Medical Diagnostics", Tibtech, 8, 161–168, June, 1990).

Chemical sensors and biosensors provide rapid response, real time monitoring of the sample/sensor interaction to produce an electronically quantified result. A chemical or biomolecular component of the sensor is used to recognize the analyte of interest. These recognition components include molecules such as antibodies, enzymes, lectins, hormones, DNA, and neuro-transmitter receptors. For example, when antibodies are used to recognize the appropriate antigens, the device can be referred to as an immunosensor. Typically, the recognition or binding of antibodies and antigens is a chemical reaction with very high equilibrium association constant. For chemical detection, the chemical reaction may have irreversibly altered or contaminated the device. The sensors are usually not reusable; they are used once and then discarded. Therefore, a suitable device must provide for easy replacement of the sensor portion, and the sensor must be inexpensive and easy to manufacture.

Devices for obtaining a quantitative result from the binding reaction have used techniques such as electrochemical, piezoelectric, capacitance, and optical detection schemes. One type of optical device uses surface plasmon resonance for measurement and is characterized by use of a metallic or metal-like film that interacts with the light in a manner that varies with the angle of light beam incidence. Another type of optical device, often referred to as evanescent wave type, requires the use of a fluophor such as fluorescein and measures resultant fluorescent radiation. Such sensors typically comprise flat plates or the surface of cylindrical rods as reviewed by Bluestein, et al.

Another class of sensors, known as distal tip sensors, use optical fibers to convey light to the distal end where the reaction is monitored by reflected light from light scattering or fluorescence from fluophors.

Optical fibers have been used in devices to measure the density of protein in blood as described by Minekane in Japanese patent 56-107419, issued Aug. 25, 1981, for a Densitometer (Application 55-9304). The fiber dipped in the sample is in the shape of a U, with the core exposed at the bent bottom. Light leaks from the exposed core depending on the concentration of protein, and the reduced light intensity that is transmitted is compared to the initial light intensity. It is well known that the leakage of light from an optical fiber depends on the radius of curvature and the index of refraction of the medium adjacent the fiber such as the cladding or the liquid sample in contact with the exposed fiber core. In such devices, which comprise a form of refractometer, the flexible unsupported fiber can have only a short length of the fiber exposed to the liquid while maintaining a fixed curvature. The limited exposed area precludes adaptation of this technique to immunoassay requiring a coating of antibodies on a significant area of the optical fiber. One typical embodiment of the present invention provides a novel way of adapting the principle of leaky fibers to planar integrated optic devices for immunoassay.

The current known technology for fabricating integrated optical devices in the form of channel waveguides is adequate for producing small optical devices by mass production techniques using photolithography and microfabrication. Such technology is applicable to typical embodiments of the present invention directed to accurate, low-cost, replaceable sensors.

Integrated optical transducers comprising channel waveguides in the form of Mach-Zehnder interferometers are known. Johnson (U.S. Pat. No. 4,515,430) discloses such an interferometer for measurement of temperature. Arms of unequal length in the interferometer utilize the temperature dependent coefficient of expansion of waveguides. Fabricius, et al (German patent DE 3,814,844, European patent 340,577) disclose an interferometer comprising a reference arm covered with substrate and an exposed measurement arm for measuring the refractive index of liquids. Means for compensating the effect of variation in source light intensity are not disclosed. The exposed waveguide arm does not contain a coating for reaction with components of the liquid sample as required for immunoassay and as in some typical embodiments of the present invention nor is there nonspecific effect compensation.

Another type of integrated optic device, the directional coupler, is employed in typical embodiments of this invention and provides for detection of properties of a fluid by measuring the index change and in some embodiments compensating for non-specific effects. Such devices have not previously been considered for use in measurement of liquid properties or chemical reactions.

BRIEF DESCRIPTION OF THE INVENTION

Typical embodiments of the apparatus useful in determining the properties of a fluid, include: means for directing light to an input portion of optical sensing means having, means for transmitting the light to replaceable optical means responsive to index of refraction in a predetermined sensing region thereof that is exposed to the fluid, means for transmitting a first predetermined portion of the light via a compensating path that includes the predetermined sensing region to first detecting means, means for transmitting a second predetermined portion of the light via a sensing path that includes the predetermined sensing region to second detecting means, and means for receiving an output from each detecting means and providing a signal responsive to the ratio of the outputs; wherein nonspecific effects are compensated.

In some typical embodiments the replaceable optical means comprises a plurality of channel waveguide means in directional coupling arrangement. In other embodiments the channel waveguide means are adjacent and substantially parallel over a predetermined region, one of them being in the compensating path and another being in the sensing region of the sensing path. In other embodiments the waveguide means in the sensing region comprises a sensing superstrate that can react with the fluid and a compensating superstrate that can react with the fluid.

In still other embodiments the sensing superstrate comprises antigen or antibody, having an index of refraction that changes in response to a binding reaction of antibody or antigen, and the compensating superstrate comprises inactivated antigen or antibody having an index of refraction that changes in response to nonspecific effects.

In some typical embodiments the replaceable optical means comprises a plurality of channel waveguide means in an interferometer arrangement. In other embodiments both arms of the interferometer pass through the sensing region and a first arm comprises a coating that can react with the fluid for measuring properties thereof and a second arm comprises a coating that can react with the fluid for compensating for nonspecific effects. In some of these embodiments the input means to the interferometer comprises a directional coupler having means for biasing the directional coupler, and the output means for the interferometer comprises a directional coupler.

In another embodiment the replaceable optical means comprises ridge waveguide means having at least two serpentine paths that pass through the sensing region and a first path comprises a coating that can react with the fluid for measuring properties thereof and a second path comprises a coating that can react with the fluid for compensating for nonspecific effects. In a smaller embodiment the replaceable optical means comprises U-bend waveguide means having at least two paths that pass through the sensing region and a first path comprises a coating that can react with the fluid for measuring properties thereof and a second path comprises a coating that can react with the fluid for compensating for nonspecific effects, or the replaceable optical means comprises S-bend waveguide means having at least two paths that pass through the sensing region and a first path comprises a coating that can react with the fluid for measuring properties thereof and a second path comprises a coating that can react with the fluid for compensating for nonspecific effects.

In a yet further typical embodiment of the invention, apparatus useful in determining properties of a fluid, comprises a substrate with an optical directional coupler integrated therein having, a first optical waveguide with a first end for receiving or exiting light and a second end for receiving or exiting light, a second optical waveguide with an end for receiving or exiting light, the first and second optical waveguides having portions which are positioned close together over an interaction length L, so that light in the first waveguide evanescently couples into the second waveguide or vice versa, and a first superstrate of known and constant index of refraction covering the first optical waveguide except for the interaction length L, and covering the second waveguide except for the interaction length L; wherein the interactive length L of the first waveguide is covered by a second superstrate that can react with the fluid; and wherein the interactive length L of the second waveguide is covered by a third superstrate that can react with the fluid. The embodiment may include a second superstrate comprising antigen or antibody, having an index of refraction that changes in response to a binding reaction of antibody or antigen and the third superstrate comprises inactivated antigen or antibody.

Another typical embodiment of the apparatus of the invention useful in determining the properties of a fluid, comprises a substrate with an optical directional coupler integrated therein having, a first optical waveguide with a first end for receiving or exiting light and a second end for receiving or exiting light, a second optical waveguide with a first end for receiving or exiting light and a second end for receiving or exiting light, the first and second optical waveguides having portions which are positioned close together over an interaction length L, so that light in the first waveguide couples into the second waveguide or vice versa, a channel means between the waveguides in an interaction length L whereby the coupling between the waveguides but above the substrate is enhanced, a first superstrate of known and constant index of refraction covering the first and second optical waveguide except for the channel in interaction length L. Other embodiments may have the channel etched into the substrate between the first and second waveguides. Still further embodiments have a channel between the first and second waveguides raised at least partially above the surface of the substrate. Yet other embodiments comprise a Y-directional coupler for providing light to the first and second light receiving waveguide ends.

Another typical embodiment useful in determining the properties of a fluid, comprises a substrate with an optical directional coupler integrated therein having a first optical waveguide with a first end for receiving or exiting light and a second end for receiving or exiting light, a second optical waveguide with a first end for receiving or exiting light and a second end for receiving or exiting light, the first and second optical waveguides having portions which are positioned close together over an interaction length L1, so that light in the first waveguide couples into the second waveguide or vice versa, a third optical waveguide with a first end for receiving or exiting light and a second end for receiving or exiting light, the third and second optical waveguides having portions which are positioned close together over an interaction length L2, so that light in the third waveguide couples into the second waveguide or vice versa, a first channel means between the first and second waveguides in an interaction length L1 whereby the coupling between the waveguides but above the substrate is enhanced, a second channel means between the third and second waveguides in an interaction length L2 whereby the coupling between the waveguides but above the substrate is enhanced. Another embodiment thereof comprises a first superstrate of known and constant index of refraction covering the first and second optical waveguide except for the channels in interaction lengths L1 and L2. While another embodiment thereof comprises a first superstrate of known and constant index of refraction covering the first and second and third optical waveguides except for the first, second, and third waveguide portions within the interaction lengths L1 and L2. A yet further embodiment comprises a first superstrate of known and constant index of refraction covering the first and second and third optical waveguides except for the first, second, and third waveguide portions, and the first and second channels within the interaction lengths L1 and L2. Other embodiment can include uncovered portions of the first waveguide and first channel that are covered by a second superstrate that can react with the fluid and wherein uncovered portions of the third waveguide and second channel are covered by a third superstrate that can react with the fluid; or embodiments wherein the uncovered portions of the first waveguide and first channel are covered by a second superstrate that can react with the fluid and wherein uncovered portions of the third waveguide and second channel are covered by a third superstrate that can react with the fluid: or wherein the uncovered portions of the first waveguide and first channel are covered by a second superstrate that can react with the fluid and wherein uncovered portions of the third waveguide and second channel are covered by a third superstrate that can react with the fluid. Another embodiment includes apparatus wherein the third superstrate is capable of providing predominantly nonspecific binding reactions.

Another typical embodiment of the invention includes apparatus useful in determining the properties of a fluid, comprising: a substrate with an optical directional coupler integrated therein having, a Y-split coupler having a first optical waveguide with an end for receiving light and second and third optical waveguides with ends for exiting light, a fourth optical waveguide with a first end for receiving or exiting light and a second end for receiving or exiting light, the second and fourth optical waveguides having portions which are positioned close together over an interaction length L1, so that light in the second waveguide couples into the fourth waveguide or vice versa, a fifth optical waveguide with a first end for receiving or exiting light and a second end for receiving or exiting light, the third and fifth optical waveguides having portions which are positioned close together over an interaction length L2, so that light in the fifth waveguide couples into the third waveguide or vice versa, a first channel means between the second and third waveguides in the interaction length L1, a second channel means between the third and fifth waveguides in the interaction length L2. Other embodiments include apparatus comprising a first channel means between the second and third waveguides in an interaction length L1 whereby the coupling between the waveguides but above the substrate is enhanced and a second channel means between the third and fifth waveguides in an interaction length L2 whereby the coupling between the waveguides but above the substrate is enhanced.

DRAWINGS

Figure 5A:
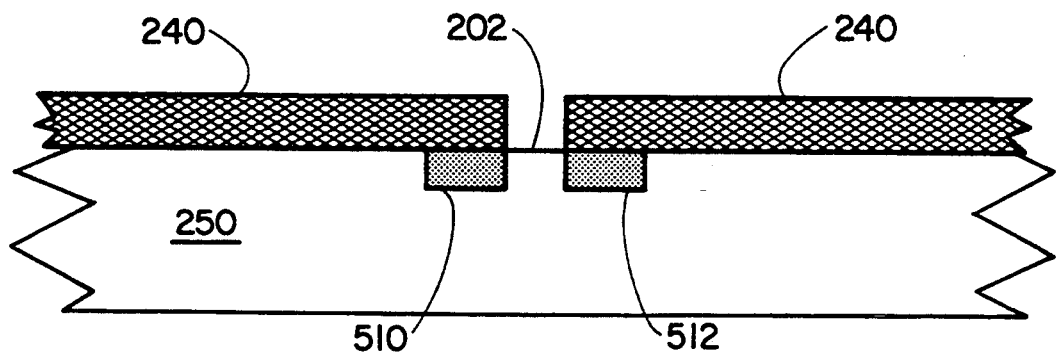
Figure 5B:
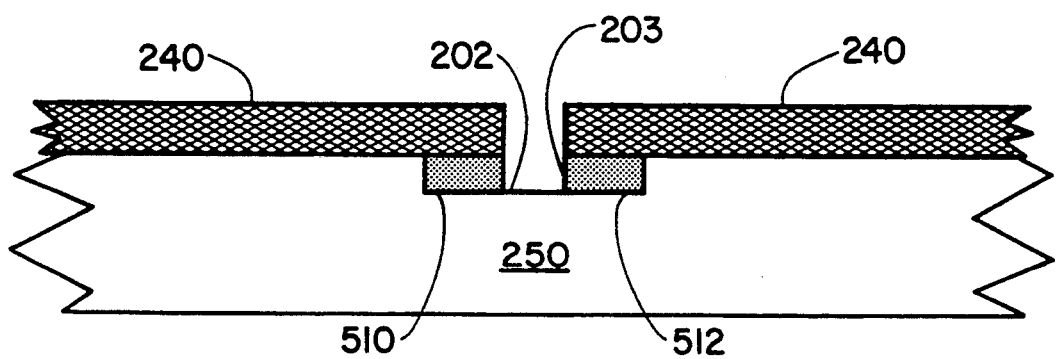
Figure 5C:
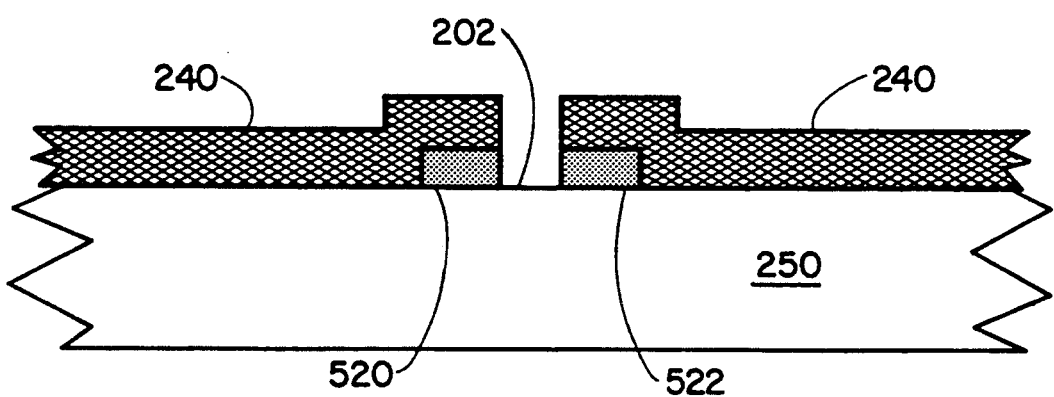

FIGS. 5A, 5B, and 5C are schematic cross-sectional views of Kappa directional couplers for some embodiments of the invention. FIG. 5A depicts a Kappa coupler with ion-exchange (embedded) waveguides. FIG. 5B depicts a Kappa Coupler with an etched region between waveguides.

Figure 6A:
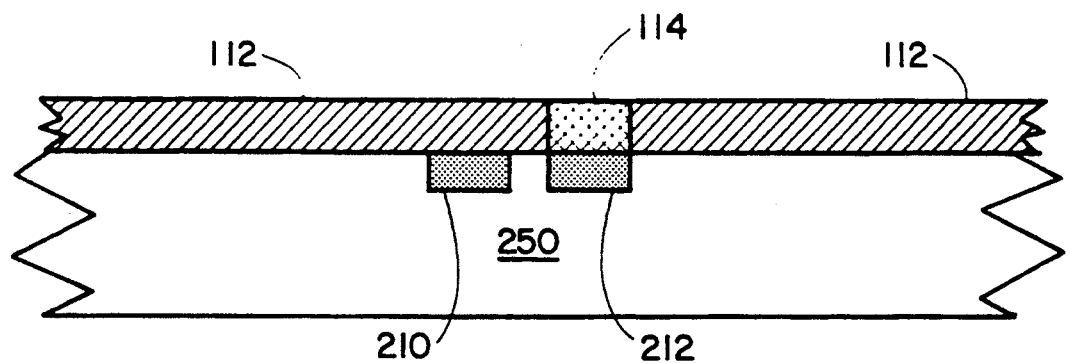
Figure 6B:
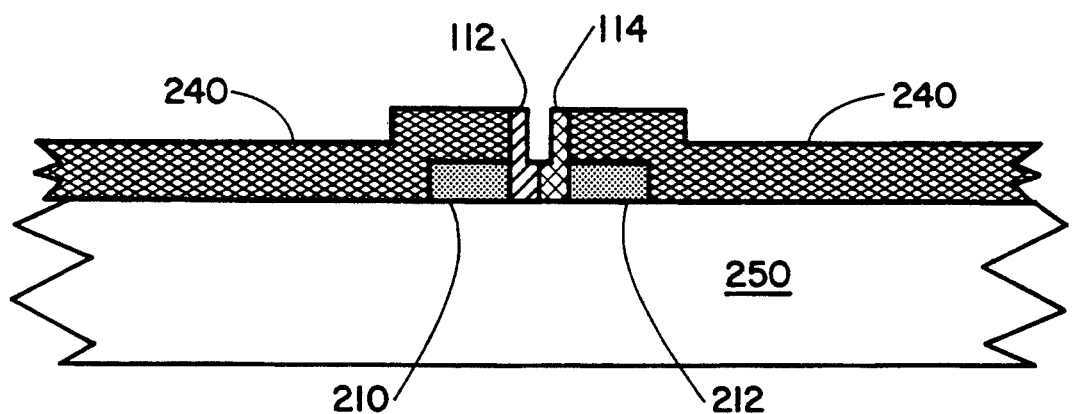
Figure 6C:
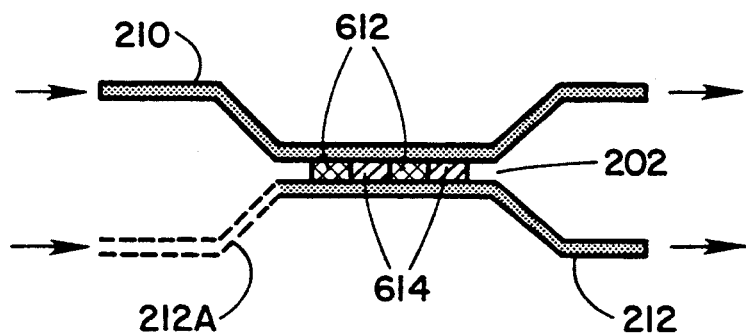

FIGS. 6A, 6B and 6C are schematic cross-sectional views showing directional coupler configurations that provide for the cancellation of nonspecific effects. FIG. 6A depicts one configuration for cancelling nonspecific effects (index change directional coupler). FIG. 6B depicts one configuration for cancelling nonspecific effects for a Kappa coupler. FIG. 6C depicts another configuration (alternating strips) for cancelling nonspecific effects for a Kappa coupler.

Figure 7A:
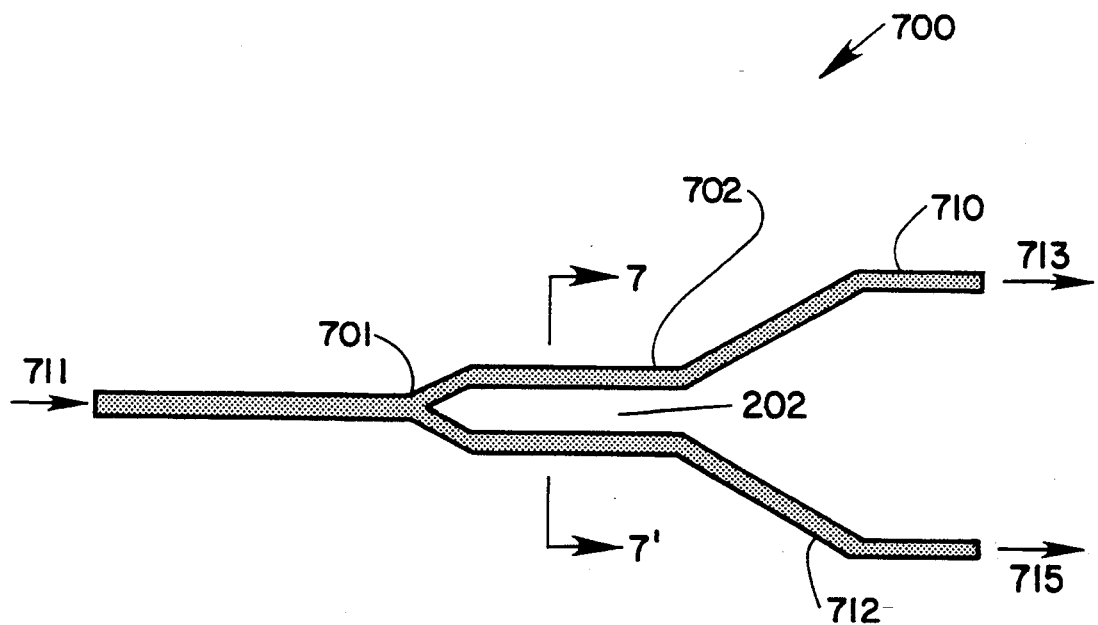
Figure 7B:
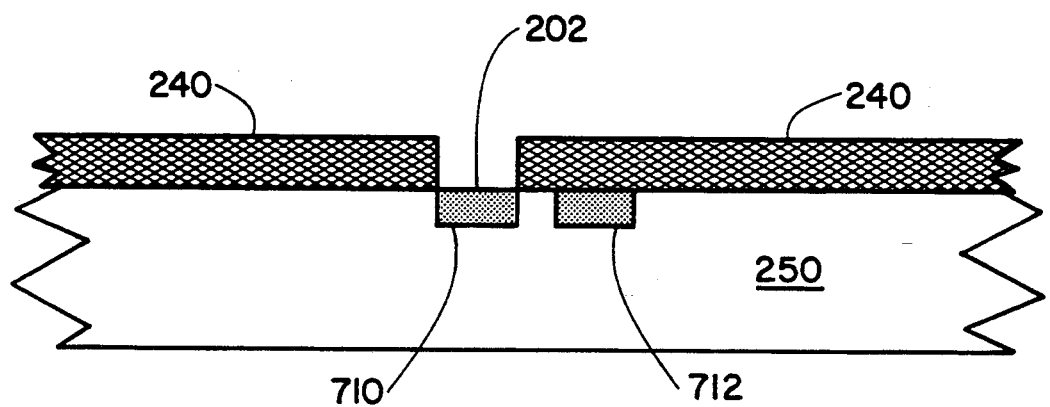

FIG. 7A illustrates a general embodiment of a Y-split directional coupler design. FIG. 7B illustrates a cross sectional view along plane 7-7', of FIG. 7A of the double guide region of the Y-split directional coupler design.

Figure 8:
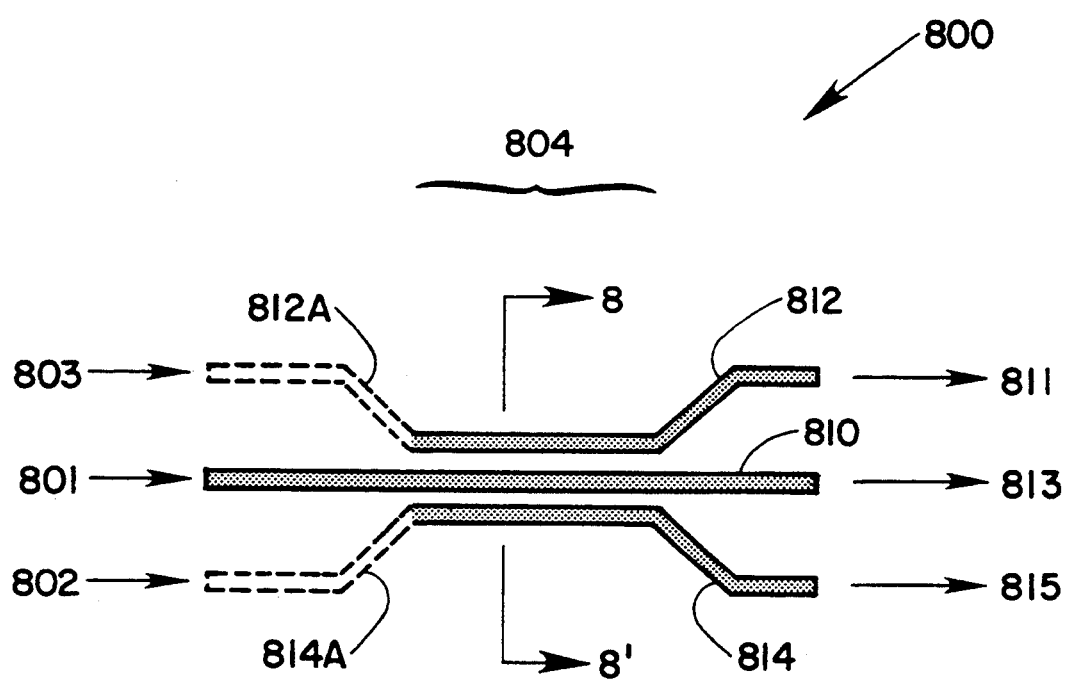

FIG. 8 illustrates a general embodiment of a double directional coupler design.

Figure 9A:
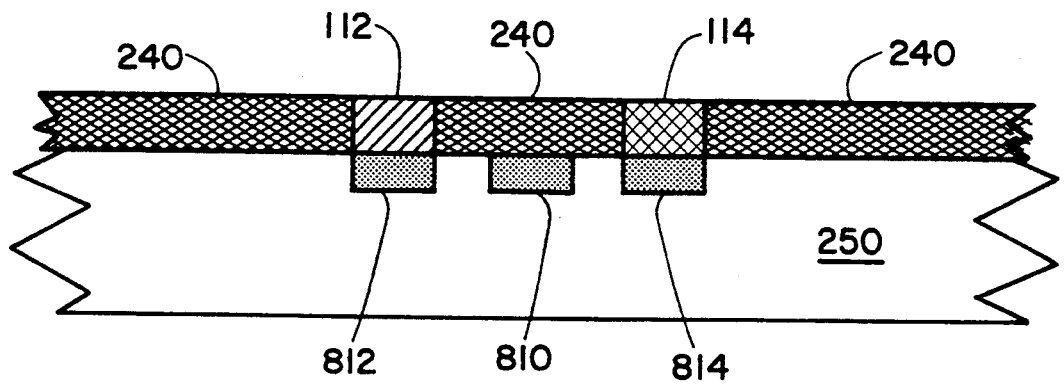
Figure 9B:
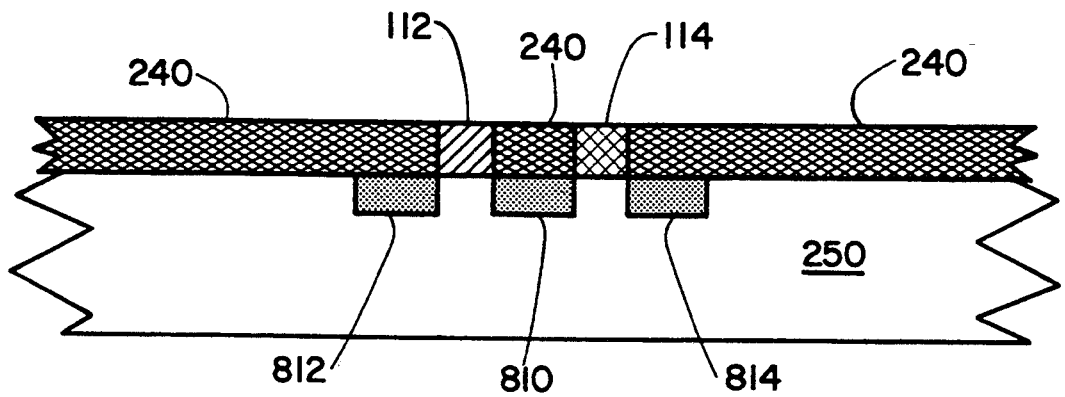
Figure 9C:
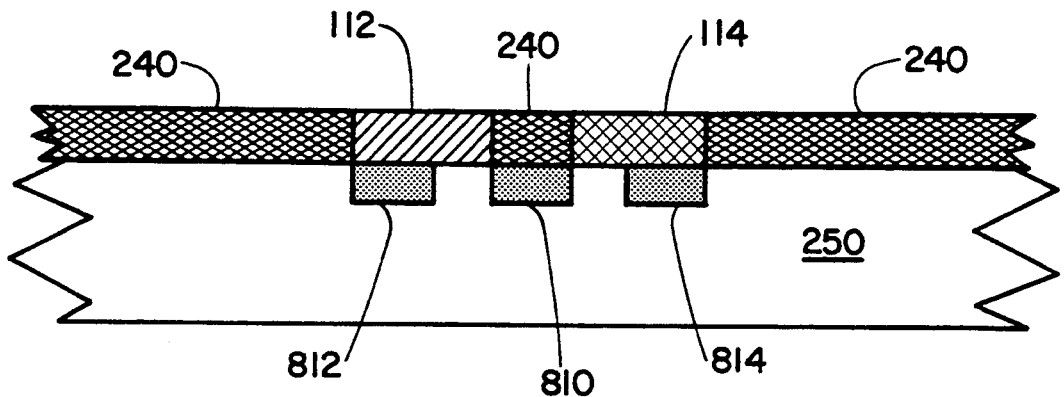

FIGS. 9A, 9B, 9C illustrate cross sectional views along plane 8-8', of the triple guide region 804 of the double directional coupler design. FIG. 9A illustrates an embodiment for canceling nonspecific effects (index change double directional coupler). FIG. 9B illustrates another embodiment for canceling nonspecific effects (double Kappa (K) coupler). FIG. 9C illustrates still another embodiment for nonspecific binding cancellation (double $\kappa+\Delta n$ coupler).

Figure 10A:
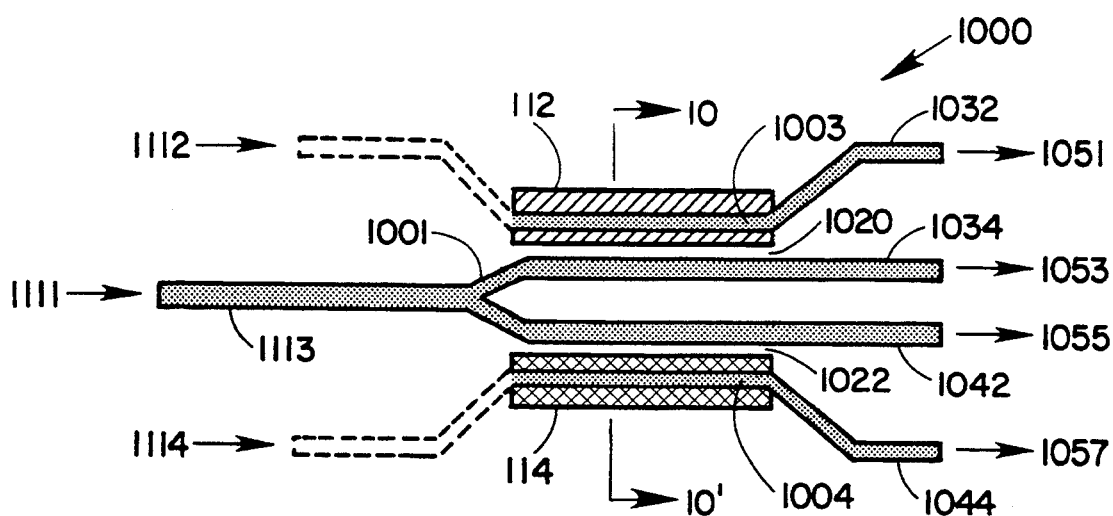

FIG. 10A illustrates one embodiment of a Y-split, double directional coupler design.

Figure 10B:
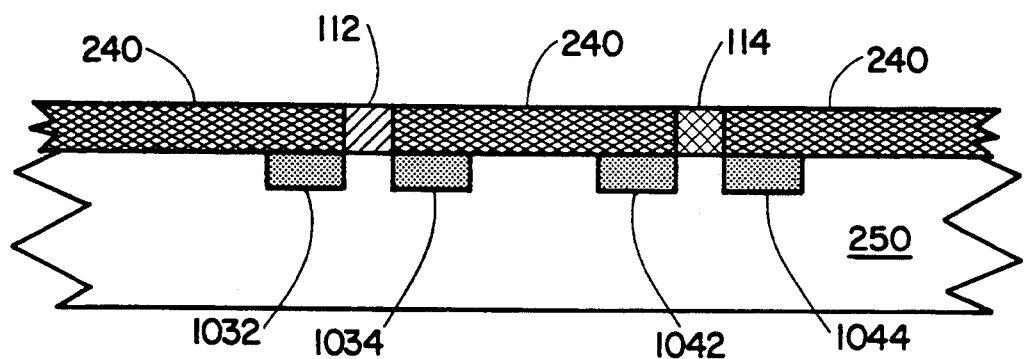
Figure 10C:
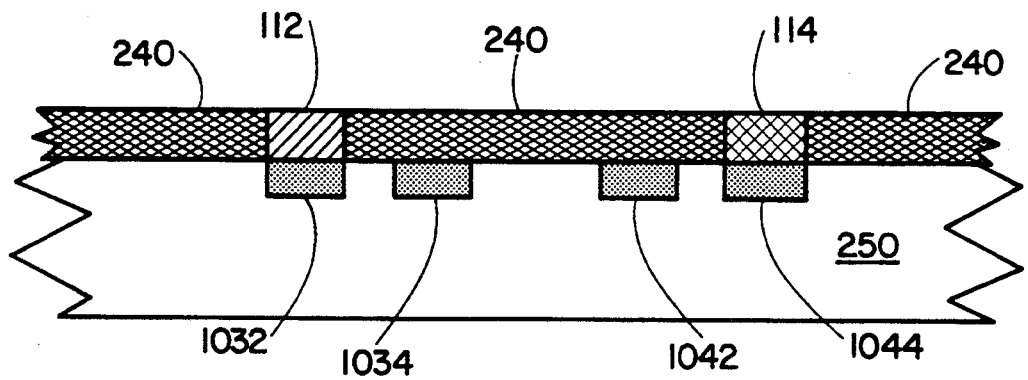

FIG. 10B and 10C illustrate embodiments for cancelling nonspecific binding effects. Cross sectional views are taken in the plane 10-10'.

Figure 11:
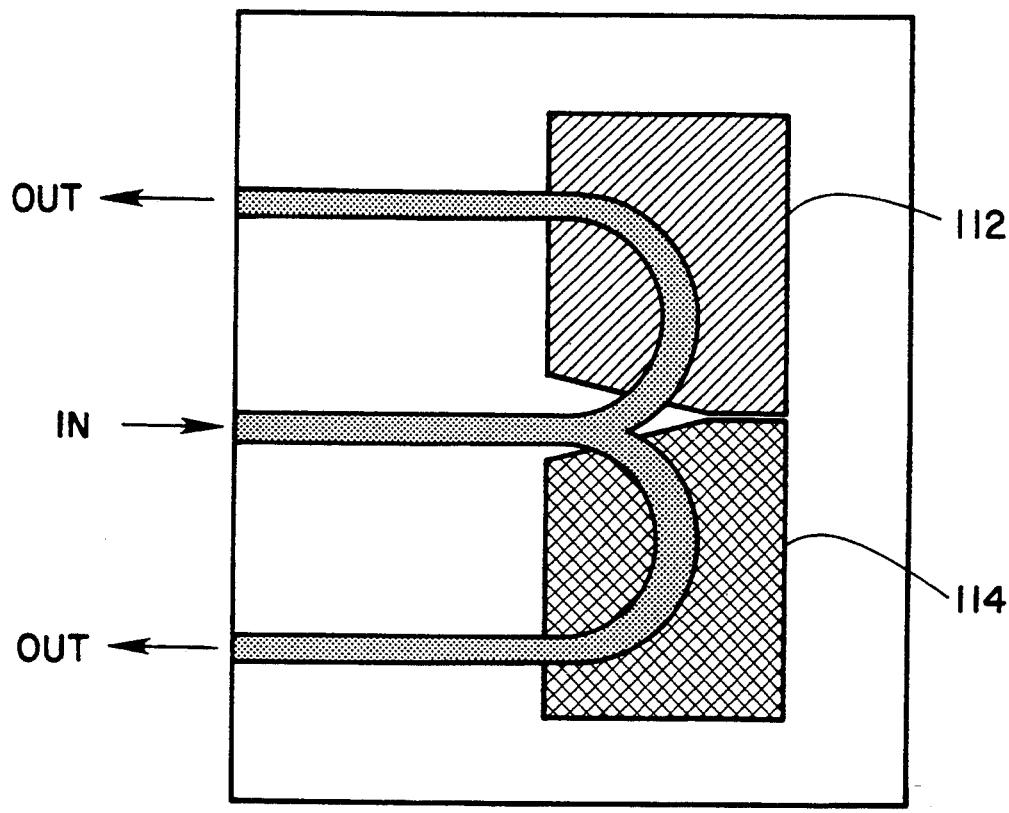

FIG. 11 Illustrates one embodiment of a U-bend, single-mode loss sensor design.

Figure 12:
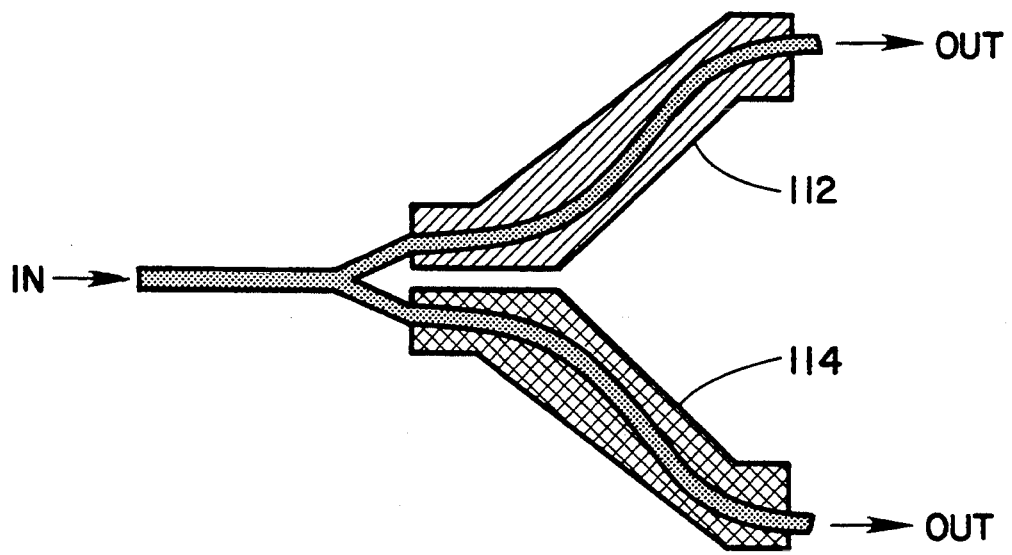

FIG. 12 illustrates one embodiment of a S-bend, single-mode bend loss sensor design.

DETAILED DESCRIPTION OF THE INVENTION

Mach-Zehnder Improvements

There are several deficiencies in the standard M-Z biorefractometer as taught by previous patent art, namely:

Variable bias from one device to another (poor sensor-to-sensor repeatability), and Nonspecific effects (absorption, scattering, index change, and Ag binding that is nonspecific) which can cause errors in output.

These deficiencies can be corrected by the present invention as discussed below.

Optical Bias Approach

Figure 1A:
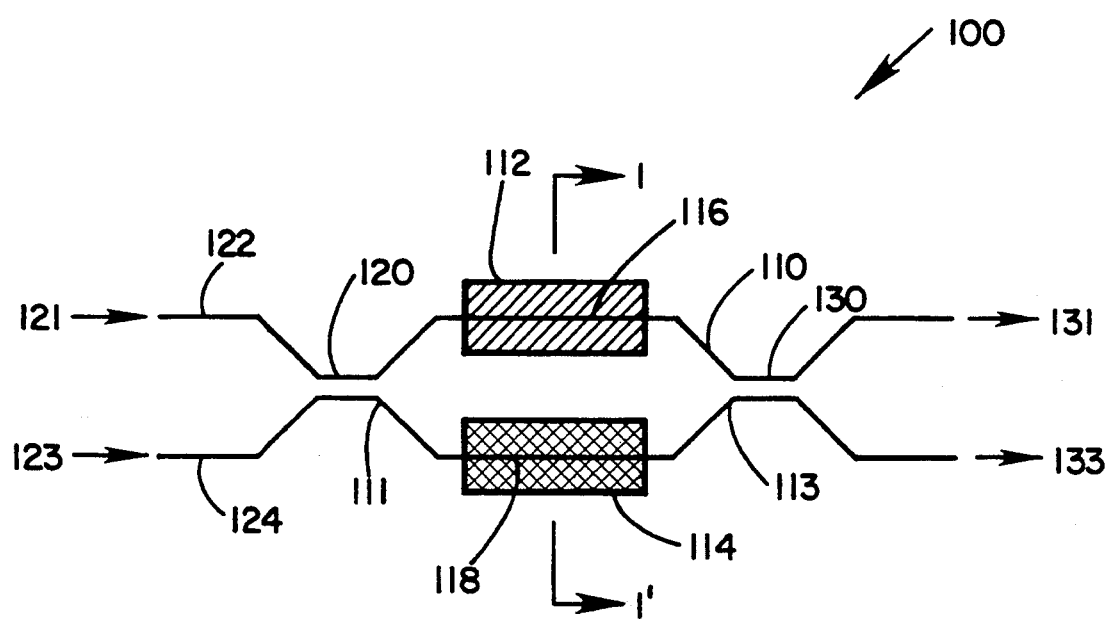
FIG. 1A is a schematic plan view representation of typical apparatus according to one embodiment of this invention with an integrated Mach-Zehnder (M-Z) optic sensor with which nonspecific binding effects can be compensated.

The variable bias problem can be addressed by using the M-Z compensated configuration 100 shown in FIG. 1A (See U.S. Pat. No. 4,989,979). In this case a M-Z interferometer 110 and two directional couplers 120, 130 are used (one at input 111 and one at output 113 of interferometer 110) instead of the standard Y-splitter and Y-coupler to provide an optical bias technique. A primary input beam 121 is introduced into one arm 122 of the input directional coupler 120. This primary beam 121 is the main sensor input. However, a second beam 123 (i.e., bias input beam) is introduced into the second coupler arm 124. The coherence of this bias beam 123 should be the same as the primary beam 121. By varying the intensity and/or phase of the bias beam 123, a common bias point can be obtained for each M-Z device 100 prior to sample introduction.

The bias adjustment procedure would work as follows: After insertion of the M-Z device 100 into a measuring instrument the primary and bias beams 121, 123 would be introduced into the M-Z interferometer 100 via the input directional coupler 120. The bias beam 123 intensity and/or phase would then be adjusted to obtain a preset bias output (independent of initial sensor bias). The sample would then be introduced and the change in sensor output noted.

Optical biasing provides another advantage—namely the ability to use quadrature techniques to extend the dynamic range of the M-Z approach. In a standard M-Z device, the output, I/Io, varies cyclically as:

$$I/Io = 0.5 \,(1 + \cos(\Delta\phi)) \tag{1}$$

where $\Delta\phi$ is the phase change caused by index changes over the arms. For large changes in index of the coating 112 (due to high analyte concentrations), the M-Z interferometer 110 output could pass through one or more cycles. Tracking this multi-cycle output change is difficult and cumbersome. However, using the optical bias approach this cycle tracking may not be necessary. The bias beam 123 intensity is simply adjusted appropriately to keep the M-Z interferometer 100 output constant (i.e., in quadrature). By monitoring the changes in optical bias required to maintain quadrature, the phase change can be measured unambiguously over many M-Z cycles (i.e. large $\Delta\phi$). Choosing the correct quadrature point can also assure that the sensor is at a point of maximum sensitivity to changes in chemistry or Ab-Ag binding.

It is also valuable to use an optional second directional coupler 130 at the interferometer output 113. This second coupler 130 provides two complementary outputs 131, 133 which can be ratioed to eliminate source intensity fluctuations.

Nonspecific Effects

Nonspecific effects can be canceled using a special modification to the M-Z interferometer 100 as shown in FIG. 1A for an embodiment for antigen detection. In this figure, note that antibody molecules (Ab's) are first attached to both arms 116, 118 of the interferometer 100 (no buffer layer is used as taught in previous patent art). The reference arm 118 of the interferometer 100 is then irradiated with ultraviolet light through a photo mask. This irradiation deactivates the antibody to produce an Ab* layer 114 on reference arm 118. Because of the deactivation, specific binding by the antigert (anti-Ab) will not occur on the second arm 118. Therefore, specific binding only occurs on the active interferometer arm 116. All other effects occur on both arms 116, 118. Since the M-Z interferometer 100 measures a change in index between the two arms, only the change due to specific binding will cause a change in M-Z output. All other (i.e., nonspecific) effects will be canceled.

Figure 1B:
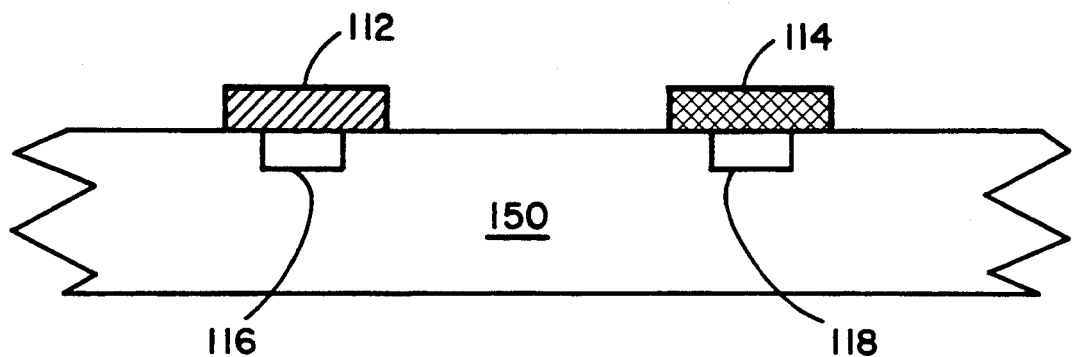
FIG. 1B is a schematic cross-sectional view, taken in the plane 1-1', of a portion of the apparatus in FIG. 1.

Referring now to Figure 1B which shows a schematic cross-sectional view, taken in the plane 1-1', of a portion of the apparatus in FIG. 1A. Substrate 150 has waveguide arms 116, 118. As described above the entire surface may be covered by antibody Ab layer 112 with deactivated antibody Ab* region 114 only over the waveguide arm 118.

Index Change Directional Coupler Data

Figure 2A:
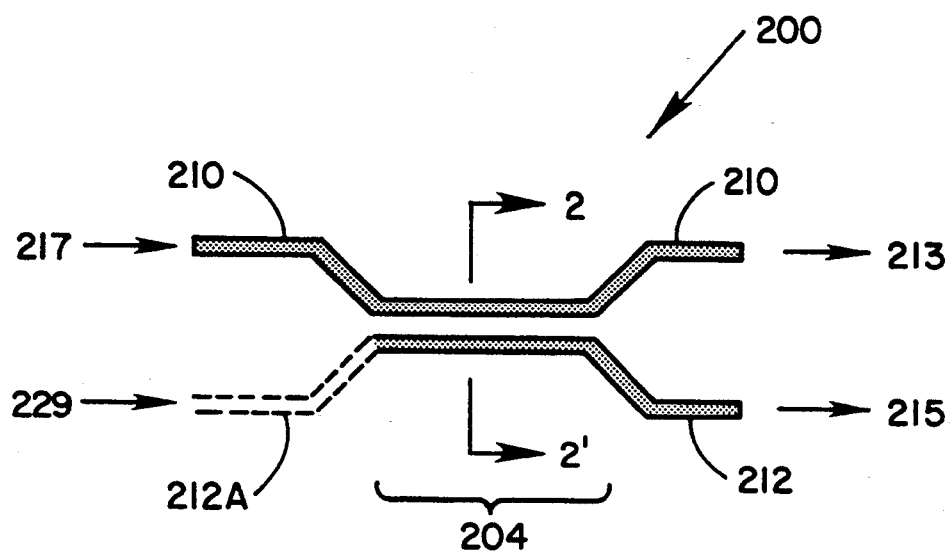
FIG. 2A is a schematic plan view of a typical planar sensor with optical waveguides in a directional coupler arrangement as included in some typical embodiments of the invention.
Figure 2B:
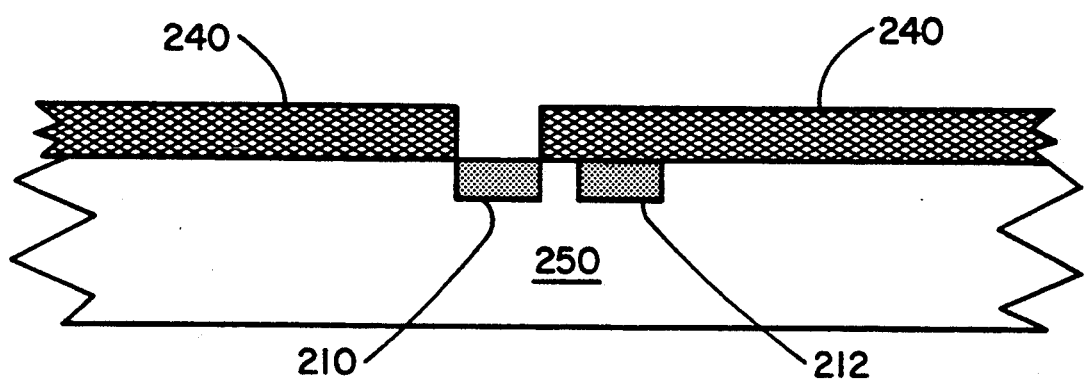
FIG. 2B is a schematic cross-sectional view, taken in the plane 2-2', of a portion of the sensor in FIG. 2.

The index change directional coupler configuration was tested by fabricating a directional coupler structure 200 as shown in FIGS. 2A and 2B. The waveguides 210, 212 were 4 $\mu$m wide and the coupling region 204 incorporated two waveguides 210, 212 separated by a 4 $\mu$m space. The length, L, of the coupling region 204 was 3 mm. Waveguide arm 212A is optional and is used when bias or other input is desired to the directional coupler 204.

As shown in FIG. 2B in the sectional side view along 2-2' of the coupling region 204, a glass buffer layer 240 was placed over substrate 250, and waveguide 212 in the coupler region 204 except over one waveguide 210 within the two waveguide light coupling region 204.

Light was coupled into the first waveguide 210 of the directional coupler 200 using a standard coupling prism technique. Both output beams 213, 215 of the coupler 200 were recorded using an optical multi-channel analyzer. Water was used as a base liquid and various index liquids were also placed over the coupling region 204 that had an index close to water. The index difference is given by:

$$\Delta n = n(liquid) - n(water) \tag{2}$$

Figure 3:
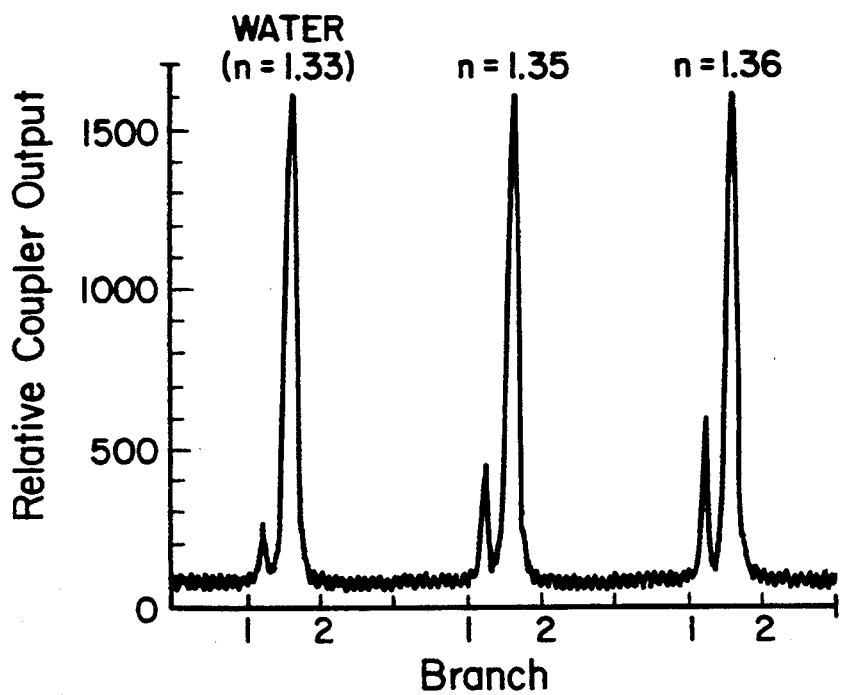
FIG. 3 is a graph showing the relative output light intensity in coupled waveguides as in FIG. 2 and 2A, as a function of liquid index changes from about 1.333 (water) to about 1.360 ($\Delta n=0.027$).

FIG. 3 shows output intensities from the two branches of the directional coupler 200 as the liquid index changes from 1.333 (water) to 1.360 ($\Delta n = 0.027$). Note that the intensity of one branch decreases slightly (#2) and the intensity of the complementary branch (#1) increases as the index difference increases. These changes are also shown in the data plotted in FIG. 4.

Figure 4:
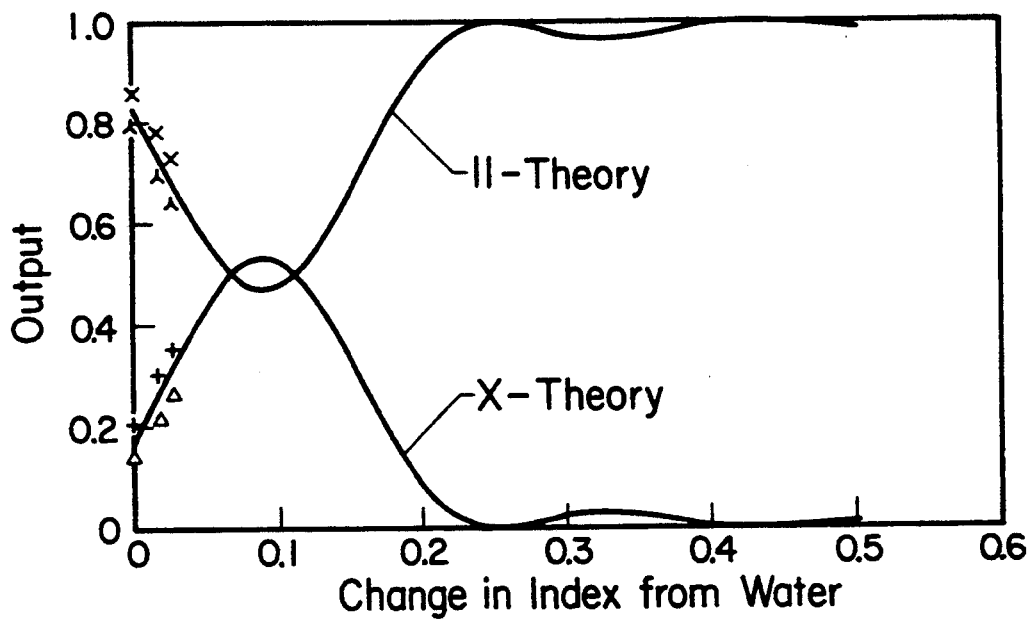
FIG. 4 is graph showing the relative light output intensity of the data from FIG. 3 and calculated output changes for the changes in index from water.

FIG. 4 also shows the calculated output change for changes in index from water.

The theoretical model computes the coupler output as a function of the following parameters:
- $\Delta l$—Deviation from coupling zone length of 3 mm (not known)
- $\kappa$—Coupling coefficient (not known)
- $\Delta n/\Delta n_{eff}$—Device efficiency (not known)
- n1—Effective index of waveguide 1 (n: 1.53090)
- n2—Effective index of waveguide 2 (not known)

Each of the four unknown parameters is altered over a wide range of values and the coupler outputs are calculated. The solution of the theoretical fit is the smallest merit function from all the iterations. The merit function is the sum of the squares of the difference between the theoretical value and the experimental value of coupler output. Note in FIG. 4 that for the following:
- $\Delta l = 0.4$ mm
- $\kappa = 240$
- $\Delta n/\Delta n_{eff} = 0.0011$
- n2 = 1.53080, the experimental and theoretical results are in best agreement. These results indicate that the basic efficiency of the directional coupler 204 (ability to measure index changes) is similar to that of a M-Z interferometer device. However, the data in FIG. 4 show that the slope of output versus index change is less than the M-Z case. Table 1 quantities the difference in slope and provides an estimate of true device sensitivity to index change.

General Advantages of Directional Coupler

The key disadvantages of the prior art Mach-Zehnder (M-Z) design (described earlier) are:

Lack of self-bias (i.e., $\Delta\phi o$ varies between the two arms for each device fabricated and coated). Therefore, the initial intensity output will be slightly different (See Equation 1). Furthermore, the initial device output may be at a peak or trough in the cos ($\Delta\phi$) curve. At these points, the device sensitivity is poor. The most desirable initial phase would be $\pi/2$ (quadrature point) where the device sensitivity is maximum.

The M-Z device output can change with changing input laser intensity and changing amounts of absorption or scattering loss in the arms (nonphase change, nonspecific effects). Because the M-Z has only one output, these nonspecific effects are not normally canceled.

These disadvantages were mitigated by using the improved M-Z design shown in FIG. 1. Optical biasing and a complimentary (second) output provided for the improved design.

Another method of overcoming the M-Z design deficiencies is to use a directional coupler architecture as shown in FIG. 2. In this case, two outputs are provided such that the following ratio can be formed:

$$Ratio = (I1-I2)/(I1+I2) \qquad (3)$$

TABLE 1

| COMPARISON OF DIRECTIONAL COUPLER AND MACH-ZEHNDER INTERFEROMETER SENSITIVITY | | | |
|---|---|---|---|
| CONFIGURATION | INTERACTION LENGTH, L (mm) | SLOPE = $\Delta I/\Delta n$ | SENSITIVITY = SLOPE/LENGTH |
| DIRECTIONAL COUPLER | 3 | 5.3 | 1.8 |
| MACH-ZEHNDER | 10 | 50 | 5 |

Results in Table 1 indicate that once interaction length is factored in, the M-Z is only approximately three times more sensitive than the directional coupler for liquid index measurement. By optimizing the coupler design, the sensitivity could be improved.

Other Configurations

There are various other biosensor configurations which may provide increased sensitivity. These configurations are summarized as follows:
A) Directional Coupler
 a) coupling coefficient change ($\Delta\kappa$)
 b) index change (see copending application) + coupling change
B) Y-Split Directional Coupler
 a) index change only
C) Double Directional Coupler
 a) index change
 b) coupling coefficient change
 c) index change + coefficient change
D) Y-Split, Double Directional Coupler
 a) index change
 b) coupling coefficient change
 c) index change + coupling coefficient change
E) Single Mode Bend
 a) U-bend
 b) S-bend These devices are described in detail below.

where I1 and I2 are the complementary coupler outputs. Since the sum (I1 +I2) is constant, the above ratio tends to reduce the effects of fabrication differences. Also, any nonphase, nonspecific effects are automatically canceled in the ratio process. Therefore, the directional coupler has some inherent advantages over the simple M-Z design.

Finally, optical biasing can also be used in the directional coupler design (See FIG. 2) by introducing a bias input beam 229 into the second input waveguide 212A. Further discussion and listing of other directional coupler advantages are provided below.

Coupling Coefficient Change Directional Coupler

By changing the geometry of the coatings/buffer layers on the waveguide surface, a coupling coefficient change directional coupler (Kappa Coupler) is formed (See FIG. 5). In this case, the open space in the buffer layer is located in between the waveguides. Therefore, the index of the material between the waveguides governs the amount of light coupling that occurs between the two guides. As used herein, a Kappa coupler is defined as a directional coupler where the coupling affected by the coupler includes (1) the coupling between the two waveguides or (2) mainly the coupling between the two waveguides and the secondary effect of index difference between the two arms of the coupler.

FIG. 5A depicts a cross sectional view of the coupling region of an embodiment of a Kappa coupler for ion-exchange waveguides 510, 512, which are imbedded in the substrate 250. A buffer layer 240 covers all but channel 202. This embodiment depends mainly on the index change in the region between the waveguides 510, 512 but above the substrate. However such a sensor will not be optimally sensitive since very little light travels between the waveguides above the substrate. To obtain greater coupling efficiency (greater sensitivity), FIG. 5B shows an etched region 203 in the channel 202 between the two waveguides 510, 512. This etched groove geometry forces an even greater amount of light to travel through the changing index region in the etched region 203 of channel 202 above the substrate 250 than the embodiment of FIG. 5A.

Another Kappa embodiment is shown in FIG. 5C where raised waveguides 520, 522 are fashioned on a substrate 250. In this case, the properties of the medium between the waveguides 520, 222 (i.e. coupling region) dominates coupling between the guides.

The potential advantage of a Kappa Coupler is that it can be more efficient in measuring index changes that occur on the device surface. Therefore, it would be possible to detect lower concentrations of analyte using Ab—Ab binding effects.

The Kappa coupler must also account for nonspecific effects. FIG. 6A shows a cross sectional area of the coupling region indicates how the index-change version (see U.S. Pat. No. 5,173,747) of the directional coupler is configured to provide cancellation of nonspecific effects. However, for the Kappa coupler (see FIG. 6B) the configuration in FIG. 6A would be difficult to produce because the Ab* zone 114 must be created in such close proximity to the Ab zone 112. One way of eliminating the above difficulty is shown in FIG. 6C. In this case, an Ab layer is created between the waveguides 210, 212 in channel 202 and zones of Ab* 614 are generated between zones of Ab 612 in a stripe fashion. Nonspecific effects will be present over both zones 612, 614. However, specific binding will cause index changes only over the Ab zones 612. This arrangement will result in cancellation of the nonspecific effects. It is likely that the width of the periodic stripes may be important. In essence, an alternating strip structure is being generated in the coupling zone.

Y-Split Directional Coupler

FIG. 7A depicts another type of directional coupler called a Y-split directional coupler 700. This device consists of a Y-split coupler 701 followed by a directional coupler region 702. After the directional coupler region 702, the waveguides 710, 712 separate again to provide two well separated output beams 713, 715. A key advantage to the Y-split directional coupler 700 is that symmetry of the device causes input power 711 to be split equally, and equal power with exactly the same phase to be launched into each directional coupler guide 710, 712. Thus, the optical power level at each output waveguide is automatically set at the 3dB half-power point at zero bias (see Elec. Let., 22, p. 941, 1986). In other words, there is some degree of self biasing in this configuration as long as the two coupling waveguides 710, 712 are symmetric.

However, as soon as antibody Ab is placed on one guide and Ab* created on the second, asymmetry will occur which will alter the bias in a somewhat unpredictable way. One method of minimizing this problem is to create one asymmetric waveguide during device fabrication which would become more symmetric after Ab-Ab* coating. The final bias adjustment could be done using a focused beam of ultraviolet light to "trim" the symmetry by creating a variable number of Ab* while observing the coupler output. This process is similar to laser trimming of resistors on current electronic devices.

It should be noted that the Y-split directional coupler functions strictly only in the index change mode because the coupling coefficient, $\kappa$, is dominated by the fixed Y-splitter rather than the index in the channel between the directional coupler waveguides (see configuration in FIG. 7B showing a cross sectional view of the directional coupling area 702 along plane 7∫7'). However, for an asymmetric directional coupler (i.e., one formed when Ab is over one coupler guide and Ab* is over the other), a Kappa or Kappa plus index change coupler configuration would also function and provide a possible sensitivity improvement.

Cancellation of nonspecific effects is the same for the Y-split directional coupler as the simple directional coupler (See FIGS. 6A, 6B, 6C).

Double Directional Coupler

In the directional coupler, described immediately above and in FIGS. 7A and 7B, it was difficult to configure the device to account for nonspecific binding effects. One way to provide a simple method for canceling these effects is to use a double directional coupler 800 design shown in FIG. 8.

In this case, primary input light 801 is introduced into a central waveguide 810 which has two coupling guides 812, 814 (one on each side). An optical bias signal 802 can be introduced to waveguide 814 to provide additional biasing of the device prior to sample introduction. Light from the primary guide 810 (and the bias guide 814) will interact in the triple guide region 804 and depending on the refractive index distribution over these various guides, more or less light will be coupled in and out of the three guides 810, 812, 814. Optionally, an additional optical bias signal 803 can be introduced to waveguide 812 to provide additional biasing of the device prior to sample introduction. Light from the primary guide 810 (and the bias guides 812, 814) will interact in the triple guide region 804. Therefore, three outputs 811, 813, 815 are provided. Various ratios of these outputs can be used to cancel all nonspecific effects.

FIGS. 9A, 9B, 9C, show that configuring the waveguide Ab-Ab* zones is much easier for the double directional coupler. FIGS. 9A, 9B, 9C illustrate cross sectional views along plane 8-8' of the triple guide region 804 and show the configurations for index change, Kappa, and Kappa+index change are shown respectively. If desired etched channels or raised waveguides as in FIGS. 5B, 5C may also be used. Note that adequate distance between Ab and Ab* zones is provided in this double directional coupler configuration. In FIGS. 9A, 9B, 9C waveguides 810, 812, 814 are formed in substrate 250. A buffer layer 240 is deposited followed by a layer of antibody Ab 112 that is subsequently deactivated in selected regions to Ab* 114.

For chemical detection and compensation, a similar device and procedure of depositing two reactive layers where one senses and the other compensates may be used.

Y-Split, Double Directional Coupler

It is possible to combine the Y-split coupler with two directional couplers (one for each leg of Y-split). This Y-Split, Double Directional Coupler 1000 configuration is shown in FIG. 10. Key advantages are:

Ease of forming Ab and Ab* zones on waveguide surface for canceling nonspecific binding effects, and Four outputs provide various intensity combinations. Ratios of these intensities can be used to cancel other nonspecific effects.

In FIG. 10A, primary input light 1111 is introduced into a central waveguide 1113 which has a Y-split coupler 1001 followed by two directional coupler region 1002 where couplers 1003 and 1004 interact with waveguides 1034, 1042 from the Y-splitter 1001. There are four outputs 1051, 1053, 1055, 1057 from waveguides 1032, 1034, 1042, 1044 respectively. Coupler interaction is at channels 1020, 1022. If desired one or two biasing signals 112, 114 may be provided to waveguides 1032, 1044. A key advantage to the Y-split directional coupler 1000 is that symmetry of the device causes input power 1111 to be split equally, and equal power with exactly the same phase to be launched into each directional coupler guide 1034, 1042. Light from the split signal in guides 1034, 1042 (and if used, the bias signal 1112, 1114) will interact in the double guide region 1002 and depending on the refractive index distribution over these various guides, more or less light will be coupled in and out of the four guides 1032, 1034, 1042, 1044. Therefore, four outputs are provided.

Nonspecific binding effects can be canceled using chemically reactive coatings and antibody coatings 112, 114 similar to those in FIGS. 10B and 10C. Various ratios of the four outputs can be used to cancel all nonspecific effects. This embodiment is the one most preferred for carrying out the invention.

Single-Mode Bend Design

There are other possible biosensors that are not interferometers or couplers. One such device is a single-mode bend device as shown in FIG. 11. FIG. 11 shows a U-bend design while FIG. 12 depicts an S-bend architecture. The S-bend device should be twice as sensitive as the U-bend configuration. This curved waveguide sensor functions by a loss mechanism as light tries to negotiate a bend in the single-mode waveguide. The amount of light that is lost depends upon the index of refraction of the waveguide compared to the surrounding media. When specific binding occurs, the index changes so the amount of loss changes. By using two bends (one coated with Ab and the second coated with Ab*) other nonspecific effects can be canceled. Since two outputs are provided, ratio methods can also be employed. These embodiments work on the same principle as the serpentine waveguide of the copending application. Thus the serpentine waveguide can likewise compensate for nonspecific effects by the application of Ab* or a complementary chemical reactive layer on the uncovered portion of the waveguide 70 (see FIG. 10 of the copending application Ser. No. 07/585,438).

Two-wavelength Two Polarization Laser

It appears that using a laser that has a special output (one wavelength with parallel and one with perpendicular polarization) will have a significant benefit to all the biosensor designs. Stability, dynamic range, sensitivity may all be improved.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit or scope of the invention.

We claim:

1. Apparatus useful in determining the properties of a fluid, comprising:

means for directing light to an input portion of optical sensing means having means for transmitting the light to replaceable optical means, the replaceable optical means responsive to index of refraction in a predetermined sensing region thereof that is exposed to the fluid, wherein the replaceable optical means comprises a plurality of channel waveguide means in directional coupling arrangement, means for transmitting a first predetermined portion of the light via a compensating path that includes the predetermined sensing region to first detecting means, wherein the channel waveguide means in the sensing region comprises a compensating superstrate that can react with the fluid, means for transmitting a second predetermined portion of the light via a sensing path that includes the predetermined sensing region to second detecting means, wherein the channel waveguide means in direct coupling arrangement in the sensing region comprises a sensing superstrate that can react with the fluid, and means for receiving an output from each detecting means and providing a signal responsive to the ration of the outputs; wherein nonspecific effects are compensated.

2. Apparatus as in claim 1, wherein the sensing superstrate comprises antigen or antibody, having an index of refraction that changes in response to a binding reaction of antibody or antigen, and the compensating superstrate comprises inactivated antigen or antibody having an index of refraction that changes in response to nonspecific effects.

3. Apparatus as in claim 1, wherein waveguide in the channel waveguide means comprises raised waveguide.

4. Apparatus useful in determining the properties of a fluid, comprising:

means for directing light to an input portion of optical sensing means having means for transmitting the light to replaceable optical means, the replaceable optical means responsive to index of refraction in a predetermined sensing region thereof that is exposed to the fluid, means for transmitting a first predetermined portion of the light via a compensating path that includes the predetermined sensing region to first detecting means, means for transmitting a second predetermined portion of the light via a sensing path that includes the predetermined sensing region to second detecting means, and means for receiving an output from each detecting means and providing a signal responsive to the ration of the outputs, wherein the replaceable optical means comprises ridge waveguide means having first and second serpentine paths that form the compensating and the sensing paths respectively, wherein the first path comprises a superstrate that can react with the fluid for compensating for nonspecific effects of the fluid, and wherein the second path comprises a superstrate that can react with the fluid for measuring properties thereof.

5. Apparatus as in claim 4, wherein the sensing superstrate comprises antigen or antibody, having an index of refraction that changes in response to a binding reaction of antibody or antigen, and the compensating superstrate comprises inactivated antigen or antibody having an index of refraction that changes in response to nonspecific effects.

6. Apparatus useful in determining the properties of a fluid, comprising:
   means for directing light to an input portion of optical sensing means having
   means for transmitting the light to replaceable optical means, the replaceable optical means responsive to index of refraction in a predetermined sensing region thereof that is exposed to the fluid,
   means for transmitting a first predetermined portion of the light via a compensating path that includes the predetermined sensing region to first detecting means,
   means for transmitting a second predetermined portion of the light via a sensing path that includes the predetermined sensing region to second detecting means, and
   means for receiving an output from each detecting means and providing a signal responsive to the ration of the outputs, wherein the replaceable optical means comprises U-bend waveguide means having first and second paths that form the compensating and the sensing paths respectively, wherein the first path comprises a superstrate that can react with the fluid for compensating for nonspecific effects of the fluid, and wherein the second path comprises a superstrate that can react with the fluid for measuring properties thereof.

7. Apparatus as in claim 6, wherein the sensing superstrate comprises antigen or antibody, having an index of refraction that changes in response to a binding reaction of antibody or antigen, and the compensating superstrate comprises inactivated antigen or antibody having an index of refraction that changes in response to nonspecific effects.

8. Apparatus useful in determining the properties of a fluid, comprising:
   means for directing light to an input portion of optical sensing means having
   means for transmitting the light to replaceable optical means, the replaceable optical means responsive to index of refraction in a predetermined sensing region thereof that is exposed to the fluid,
   means for transmitting a first predetermined portion of the light via a compensating path that includes the predetermined sensing region to first detecting means,
   means for transmitting a second predetermined portion of the light via a sensing path that includes the predetermined sensing region to second detecting means, and
   means for receiving an output from each detecting means and providing a signal responsive to the ratio of the outputs; wherein the replaceable optical means comprises S-bend waveguide means having first and second paths that form the compensating and the sensing paths respectively, wherein the first path comprises a superstrate that can react with the fluid for compensating for nonspecific effects of the fluid, and wherein the second path comprises a superstrate that can react with the fluid for measuring properties thereof.

9. Apparatus as in claim 8, wherein the sensing superstrate comprises antigen or antibody, having an index of refraction that changes in response to a binding reaction of antibody or antigen, and the compensating superstrate comprises inactivated antigen or antibody having an index of refraction that changes in response to nonspecific effects.

10. Apparatus useful in immunoassay of a fluid, comprising:
    a substrate with an optical directional coupler integrated therein having,
    a first optical waveguide with a first end for receiving or exiting light and a second end for receiving or exiting light,
    a second optical waveguide with an end for receiving or exiting light,
    the first and second optical waveguides having portions which are positioned close together over an interaction length L, so that light in the first waveguide evanescently couples into the second waveguide or vice versa, and
    a first superstrate of known and constant index of refraction covering the first optical waveguide except for the interaction length L, and covering the second waveguide except for the interaction length L;
    wherein the interactive length L of the first waveguide is covered by a second superstrate that can react with the fluid, and the interactive length L of the second waveguide is covered by a third superstrate that can react with the fluid.

11. Apparatus as in claim 10, wherein the second superstrate comprises antigen or antibody, having an index of refraction that changes in response to a binding reaction of antibody or antigen and the third superstrate comprises inactivated antigen or antibody.

12. Apparatus as in claim 10, wherein the second optical waveguide comprises a second end for receiving and exiting light.

13. Apparatus as in claim 10, wherein the first and second waveguides comprise raised waveguides.

14. Apparatus useful in determining the properties of a fluid, comprising:
    a substrate with an optical directional coupler integrated therein having,
    a first optical waveguide with a first end for receiving or exiting light and a second end for receiving or exiting light,
    a second optical waveguide with a first end for receiving or exiting light and a second end for receiving or exiting light,
    the first and second optical waveguides having portions which are positioned close together over an interaction length L, so that light in the first waveguide couples into the second waveguide or vice versa,
    a channel between the waveguides in an interaction length L, wherein the coupling between the waveguides is enhanced,
    a first superstrate of known and constant index of refraction covering the first and second optical waveguide except for the channel in interaction length L.

15. Apparatus as in claim 14, wherein a channel is etched into the substrate between the first and second waveguides.

16. Apparatus as in claim 14, comprising a channel between the first and second waveguides, the waveguides being raised at least partially above the surface of the substrate.

17. Apparatus as in claim 14, comprising a Y-directional coupler for providing light to the first and second light receiving waveguide ends.

18. Apparatus as in claim 14, wherein the second optical waveguide comprises only a first end for receiving and exiting light.

19. Apparatus as in claim 14, wherein the channel is covered by alternating strips of a second superstrate and a third superstrate that can react with the fluid.

20. Apparatus as in claim 19, wherein the second superstrate comprises antigen or antibody, having an index of refraction that changes in response to a binding reaction of antibody or antigen, and the third superstrate comprises inactivated antigen or antibody having an index of refraction that changes in response to non-specific effects.

21. Apparatus as in claim 14, wherein the first and second waveguides comprise raised waveguides.

22. Apparatus useful in determining the properties of a fluid, comprising:
- a substrate with an optical directional coupler integrated therein having,
- a first optical waveguide with a first end for receiving or exiting light and a second end for receiving or exiting light,
- a second optical waveguide with a first end for receiving or exiting light and a second end for receiving or exiting light,
- the first and second optical waveguides having portions which are positioned close together over an interaction length L1, so that light in the first waveguide couples into the second waveguide or vice versa,
- a third optical waveguide with a first end for receiving or exiting light and a second end for receiving or exiting light,
- the third and second optical waveguides having portions which are positioned close together over an interaction length L2, so that light in the third waveguide couples into the second waveguide or vice versa,
- a first channel between the first and second waveguides in an interaction length L1, wherein the coupling between the waveguides above the substrate is enhanced, and
- a second channel between the third and second waveguides in an interaction length L2, wherein the coupling between the waveguides above the substrate is enhanced, and
- a first superstrate of known and constant index of refraction covering the first, second, and third optical waveguides except for first and second channels in interaction lengths L1 and L2.

23. Apparatus as in claim 22, wherein the uncovered portions of the first channel are covered by a second superstrate that can react with the fluid, and wherein uncovered portions of the second channel are covered by a third superstrate that can react with the fluid.

24. Apparatus as in claim 23, wherein the third superstrate is capable of providing predominantly nonspecific binding reactions.

25. Apparatus useful in determining the properties of a fluid, comprising:
- a substrate with an optical directional coupler integrated therein having,
- a first optical waveguide with a first end for receiving or exiting light and a second end for receiving or exiting light,
- a second optical waveguide with a first end for receiving or exiting light and a second end for receiving or exiting light,
- the first and second optical waveguides having portions which are positioned close together over an interaction length L1, so that light in the first waveguide couples into the second waveguide or vice versa,
- a third optical waveguide with a first end for receiving or exiting light and a second end for receiving or exiting light,
- the third and second optical waveguides having portions which are positioned close together over an interaction length L2, so that light in the third waveguide couples into the second waveguide or vice versa,
- a first channel between the first and second waveguides in an interaction length L1, wherein the coupling between the waveguides above the substrate is enhanced,
- a second channel between the third and second waveguides in an interaction length L2, wherein the coupling between the waveguides above the substrate is enhanced, and
- a first superstrate of known and constant index of refraction covering the first, second, and third optical waveguides except for the first and third waveguide portions within the interaction lengths L1 and L2.

26. Apparatus as in claims 25, wherein the uncovered portions of the first waveguide are covered by a second superstrate that can react with the fluid, and wherein uncovered portions of the third waveguide are covered by a third superstrate that can react with the fluid.

27. Apparatus useful in determining the properties of a fluid, comprising:
- a substrate with an optical directional coupler integrated therein having,
- a first optical waveguide with a first end for receiving or exiting light and a second end for receiving or exiting light,
- a second optical waveguide with a first end for receiving or exiting light and a second end for receiving or exiting light.
- the first and second optical waveguides having portions which are positioned close together over an interaction length L1, so that light in the first waveguide couples into the second waveguide or vice versa,
- a third optical waveguide with a first end for receiving or exiting light and a second end for receiving or exiting light,
- the third and second optical waveguides having portions which are positioned close together over an interaction length L2, so that light in the third waveguide couples into the second waveguide or vice versa, a first channel between the first and second waveguides in an interaction length L1, wherein the coupling between the waveguides above the substrate is enhanced, a second channel between the third and second waveguides in an interaction length L2, wherein the coupling between the waveguides above the substrate is enhanced, and a first superstrate of known and constant index of refraction covering the first, second, and third optical waveguides except for the first and third waveguide portions, and the first and second channels within the interaction length L1 and L2.

28. Apparatus as in claim 27, wherein the uncovered portions of the first waveguide and first channel are covered by a second superstrate that can react with the fluid, and wherein uncovered portions of the third waveguide and second channel are covered by a third superstrate that can react with the fluid.

29. Apparatus useful in determining the properties of a fluid, comprising:
- a substrate with an optical directional coupler integrated therein having,
- a Y-split coupler having a first optical waveguide with an end for receiving light and second and third optical waveguides with ends for exiting light,
- a fourth optical waveguide with a first end for receiving or exiting light and a second end for receiving or exiting light,
- the second and fourth optical waveguides having portions which are positioned close together over an interaction length L1, so that light in the second waveguide couples into the fourth waveguide or vice versa,
- a fifth optical waveguide with a first end for receiving or exiting light and a second end for receiving or exiting light,
- the third and fifth optical waveguides having portions which are positioned close together over an interaction length L2, so that light in the fifth waveguide couples into the third waveguide or vice versa,
- a first channel between the second and fourth waveguides in the interaction length L1,
- a second channel between the third and fifth waveguides in the interaction length L2, and
- a first superstrate of known and constant index of refraction covering the second, third, fourth and fifth optical waveguides except for the first channel and second channel within the interaction lengths L1 and L2.

30. Apparatus as in claim 29, wherein the waveguides comprise raised waveguides.

31. Apparatus as in claim 29, wherein the first channel in the interactive length L1 covered by a second superstrate that can react with the fluid, and the second channel in the interactive length L2 is covered by a third superstrate that can react with the fluid.

32. Apparatus as in claim 29, wherein the second superstrate comprises antigen or antibody, having an index of refraction that changes in response to a binding reaction of antibody or antigen and the third superstrate comprises inactivated antigen or antibody.

33. Apparatus as in claim 29, wherein the fourth optical waveguide comprises only a first end for receiving and exiting light, and the fifth optical waveguide comprises only a first end for receiving and exiting light.

* * * * *

UNITED STATES PATENT AND TRADEMARK OFFICE
CERTIFICATE OF CORRECTION

PATENT NO. : 5,377,008

DATED : December 27, 1994

INVENTOR(S) : Richard W. Ridgway, Anthony A. Boiarski, Van E. Wood, and James R. Busch It is certified that error appears in the above—identified patent and that said Letters Patent is hereby corrected as shown below:

Column 1, line 66, "equilibium" should be -- equilibrium --.

Column 5, line 30, "embodiment" should be -- embodiments --.

Column 6, line 61, "(K)" should be -- ($\kappa$) --.

Column 8, line 20, "antigert" should be -- antigen --.

Column 9, line 5, "$\Delta 1$" should be -- $\Delta L$ --.

Column 9, line 18, "$\Delta 1$" should be -- $\Delta L$ --.

Column 12, line 15, "7 ʃ 7')" should be -- 7-7') --.

Column 13, line 21, "112, 114" should be -- 1112, 1114 --.

Column 14, line 38, "ration" should be -- ratio --.

Column 15, line 33, "ration" should be -- ratio --.

UNITED STATES PATENT AND TRADEMARK OFFICE
CERTIFICATE OF CORRECTION

PATENT NO.   : 5,377,008
DATED        : December 27, 1994
INVENTOR(S)  : Richard W. Ridgway, et. al.

It is certified that error appears in the above-indentified patent and that said Letters Patent is hereby corrected as shown below:

Column 19, line 13, "length" should be --lengths--.

Signed and Sealed this

Eighteenth Day of April, 1995

Attest:

BRUCE LEHMAN

Attesting Officer

Commissioner of Patents and Trademarks